(12) United States Patent
Amano et al.

(10) Patent No.: US 6,659,975 B2
(45) Date of Patent: Dec. 9, 2003

(54) PLASMA COLLECTING DEVICE

(75) Inventors: Yoshikazu Amano, Saitama (JP); Toshihiro Mori, Saitama (JP)

(73) Assignee: Fuju Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/858,393

(22) Filed: May 16, 2001

(65) Prior Publication Data

US 2001/0044615 A1 Nov. 22, 2001

(30) Foreign Application Priority Data

May 16, 2000 (JP) ........................................ 2000-142734

(51) Int. Cl.[7] ............................................ A61M 31/00
(52) U.S. Cl. ........................ 604/48; 604/263; 604/197
(58) Field of Search .................. 604/48, 195, 263, 604/110, 187, 197

(56) References Cited

U.S. PATENT DOCUMENTS

| | | | | |
|---|---|---|---|---|
| 2,549,417 A | * | 4/1951 | Brown | 604/90 |
| 3,134,380 A | * | 5/1964 | Armao | 604/198 |
| 3,874,367 A | * | 4/1975 | Ayres | 600/577 |
| 4,444,203 A | * | 4/1984 | Engelman | 600/576 |
| 4,883,068 A | * | 11/1989 | Dechow | 600/573 |
| 5,051,109 A | * | 9/1991 | Simon | 604/192 |
| 5,139,685 A | * | 8/1992 | de Castro et al. | 210/435 |
| 5,589,399 A | * | 12/1996 | Allen et al. | 436/169 |
| 6,024,710 A | * | 2/2000 | Miller | 600/578 |
| 6,126,618 A | * | 10/2000 | Bischof | 600/576 |
| 6,383,818 B1 | * | 5/2002 | Arai et al. | 210/505 |

FOREIGN PATENT DOCUMENTS

JP        5-93721        * 4/1993

* cited by examiner

Primary Examiner—Gene Mancene
Assistant Examiner—Khoa D. Huynh
(74) Attorney, Agent, or Firm—Reed Smith LLP

(57) ABSTRACT

A plasma-collecting devise comprises a blood-filtering element having a blood-drawing needle and a communicating needle, a vacuum blood-drawing tube, and a contracting and expanding element connecting the blood-filtering unit and the vacuum blood-drawing tube. The device enables blood drawing from blood vessel and blood filtering continuously to obtain plasma.

8 Claims, 1 Drawing Sheet

PLASMA COLLECTING DEVICE

CROSS-REFERENCES TO RELATED APPLICATIONS

This application claims Paris Convention priority of Japanese Application No. 2000-142734 filed May 16, 2000, the complete disclosure of which is hereby incorporated by reference.

FIELD OF THE INVENTION

The present invention relates to a device for collecting plasma from blood vessel instantaneously by drawing and filtering blood continuously.

BACKGROUND OF THE INVENTION

Kind or concentration of blood components, such as metabolites, proteins, lipids, electrolytes, enzymes, antigens and antibodies, is measured, in general, using a plasma or serum sample obtained by centrifuging whole blood. However, centrifuging takes labor and time. Particularly, centrifuging is unsuitable for an urgent case of measuring a small number of samples promptly and on site inspection, because of requiring a centrifuge and electricity. Thereupon, it has been investigated to separate plasma or serum from whole blood by filtration.

Several filtration methods using glass fiber filter have been known wherein whole blood is charged into the glass fiber put in a column from one side of the column, and plasma or serum is obtained from the other side (Japanese Patent KOKOKU Nos. 44-14673, 5-52463, Japanese Patent KOKAI Nos. 2-208565, 4-208856).

However, practical filtration methods capable of obtaining an amount of plasma or serum from whole blood necessary for measuring by an automatic analyzer have not been developed except a part of items, such as blood sugar.

On the other hand, inventors belonging to the assignee of this application have developed a plasma or serum filtering unit comprising a filter element containing a combination of glass fiber filter and porous membrane and a baffle narrowing aperture of the filter element at an exit of a filtrate passage, with which plasma or serum can be separated effectively even from a small quantity of whole blood (U.S. Pat. No. 5,979,669).

Further, these inventors have developed a blood-filtering unit comprising a injection needle for drawing blood at an inlet of the blood-filtering unit and a filtrate receiver connected to an exit of a filtrate passage (U.S. Pat. No. 5,996,811).

But the unit was unsatisfactory for practical use in terms of uneasy operation or handling, since it required a sucking adaptor or syringe connected with the blood-filtering unit to collect and filter blood instantaneously.

Further, a device comprising a vacuum blood-drawing tube containing a injection needle at a front edge of it and accommodating a blood-filtering unit in it, a vacuum tube to suck in filtered serum or plasma, and a part with two injection needles connecting the vacuum blood-drawing tube and the vacuum tube has been developed to separate serum or plasma from whole blood (Japanese Patent KOKAI Nos. 4-208856, 5-93721, 5-188053).

But operation of this device is troublesome too. Because three injection needles contained in the device must be stung in correct order to connect four parts of the device.

SUMMARY OF THE INVENTION

An object of the invention is to provide a device capable of collecting plasma for analysis from blood vessel instantaneously by drawing and filtering blood continuously.

The present inventors investigated in order to solve the aforementioned problems, and they invented a plasma-collecting device comprising a blood-filtering unit having two injection needles connected to each of its two openings, a vacuum blood-drawing tube, and an expanding and contracting element connecting the blood-filtering unit and the vacuum blood-drawing tube.

After one of the injection needles stings into blood vessel, the other injection needle breaks into the vacuum blood-drawing tube by pressure to conduct suction and filtration of blood continuously. Thus, a plasma sample is obtained readily and reliably using the plasma-collecting device according to the present invention.

DETAILED DESCRIPTION OF THE INVENTION

Figure 1:
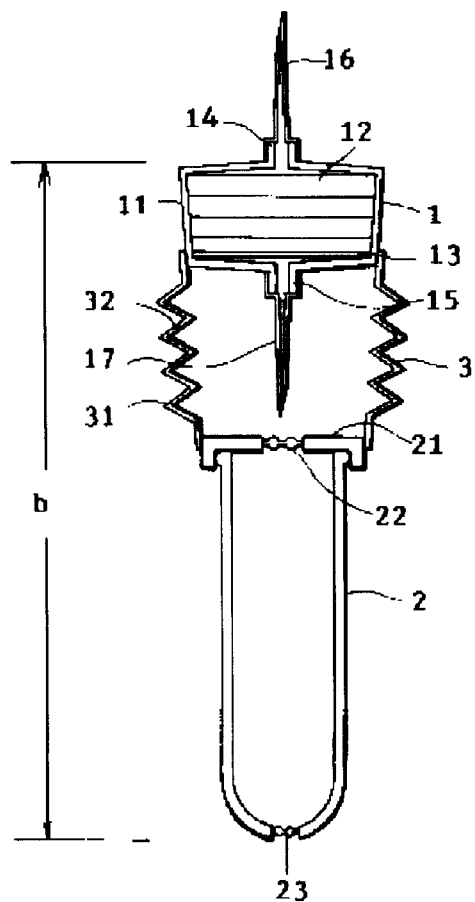
FIG. 1 is a longitudinal section of a plasma-collecting device in accordance with the present invention having a bellows 3 as an expanding and contracting element.

The blood-filtering unit used in the present invention comprises a holder having a blood inlet and a filtrate outlet and accommodating blood-filtering material.

There is no restriction of the blood-filtering material used in the invention, but it is preferable to use such material which catches to remove blood cells gradually by entangling at first large blood cell components and then smaller blood cell components in the space structure with permeating in the thickness direction in total of the filtering material, called the volumetric filtration, instead of material which trap blood cells only by the surface. Preferably glass fiber filter is used, and combination of glass fiber filter and a microporous membrane is the most preferably used.

The glass fiber filter has a density of about 0.02 to 0.5 $g/cm^3$, preferably about 0.03 to 0.2 $g/cm^3$, more preferably about 0.05 to 0.13 $g/cm^3$, and a retainable particle size of about 0.6 to 9 $\mu$m, preferably 1 to 5 $\mu$m. By treating the surface of glass fiber with hydrophilic polymer as disclosed in Japanese Patent KOKAI Nos. 2-208565, 4-208856, filtration proceeds faster and smoothly. Lectin or other reactive reagent or modifier may be incorporated into the glass fiber, or the glass fiber may be treated therewith. Two or more sheets of the glass fiber filter may be laminated.

Microporous membranes with surface being made hydrophilic and is capable of separating blood cell from whole blood separate whole blood into blood cells and plasma specifically without hemolysis to the degree of substantially influencing analytical values. A suitable pore size of the microporous membrane is smaller than the retainable particle size of glass fiber filter but is 0.2 $\mu$m or more, preferably about 0.3 to 5 $\mu$m, more preferably about 0.5 to 3 $\mu$m. A higher void content of the microporous membrane is preferable, and a suitable void content is about 40 to 95%, preferably about 50 to 95%, more preferably about 70 to 95%. Illustrative of the microporous membranes are polysulfone membrane, fluorine-containing polymer membrane, cellulose acetate membranes, nitrocellulose membrane, etc. The preferable microporous membranes are polysulfone membrane or cellulose acetate membranes. And polysulfone membrane is the most preferable.

The blood-filtering material used in the invention comprises a stack of the glass fiber filter opposed to the blood inlet and the microporous membrane opposed to the filtrate outlet. The most preferable stack is composed of the glass fiber filter and polysulfone membrane. The stack may be integrated by joining each layer using partially disposed (e.g. spots) adhesive, according to disclosures in Japanese Patent KOKAI Nos. 62-138756-8, 2-105043, 3-16651, etc.

Suitable thickness of the glass fiber filter is determined depending on the volume of plasma to be recovered, and density (or void content) and surface area of the glass fiber filter. Necessary amount of plasma or serum for analyzing plural items using dry analytical elements is 100 to 500 µl. In practical viewpoint, the glass fiber filter having a density of about 0.02 to 0.2 g/cm$^3$ and a surface area of 1 to 5 cm$^2$ is suitable. In this case, the suitable thickness of the glass fiber filter is about 1 to 10 mm, preferably about 2 to 8 mm. The above mentioned thickness can be achieved by superposing 2 to 10 sheets, preferably 3 to 8 sheets, of the glass fiber filter.

Suitable thickness of the microporous membrane is about 0.05 to 0.5 mm, preferably about 0.1 to 0.3 mm. Though necessary microporous membrane is usually one sheet, two or more sheets may be used in laminate.

The holder accommodates the blood-filtering material, and is provided with the blood inlet and the filtrate outlet. The holder is, in general, formed of a filter chamber accommodating the blood-filtering material and a cap. Both of the filter chamber and the cap have at least one aperture, respectively. One is used as the blood inlet and the other as the filtrate outlet. On the outer surface of the holder, one or two protrusions, such as flanges, may be provided as a finger hold. And concaves may be provided as a finger hold around the surface of the area on where a blood-drawing needle is fixed.

The volume of the filter chamber is necessary to be greater than the total volume of the blood-filtering material both in a dry state and in a swelled state upon absorbing a sample (i.e. whole blood). When the volume of the filter chamber is smaller than the total volume of the blood-filtering material, filtration does not proceed efficiently and hemolysis occurs. A suitable ratio of the volume of the filter chamber to the total volume of the blood-filtering material in a dry state is, in general, about 101 to 400%, preferably about 110 to 150%, more preferably about 120 to 140%, although the ratio varies according to the swelling degree of the filtering material. A practical volume of it is determined considering the desired volume of filtered plasma or serum, and is about 0.5 to 2.5 ml, typically about 0.6 to 2.2 ml.

Besides, it is necessary that the periphery of the blood-filtering material be closely fitted to the wall of the filter chamber so as not to form a bypass of whole blood without passing the blood-filtering material. But no trouble occurs if whole blood passing through the bypass is in so small volume that it is cut off by the microporous membrane.

The blood-drawing needle is firmly connected to the blood inlet of the holder to make the connection area airtight. It may be connected to the blood inlet with adhesive, by fusion welding, by being screwed or compressed in, or with a screw.

The blood-filtering unit used in the present invention is made into a closed structure after attaching the cap to the chamber except the blood inlet and the filtrate outlet, which is also used as a suction port.

The holder is preferably made of plastics. Such transparent or opaque resins as polymethacrylates, polyethylene, polypropylene, polyesters, nylon or polycarbonates may be used.

The cap may be fitted to the filter chamber with various means, such as adhesion using adhesive or fusion welding. On that occasion, either periphery of the holder body or of the cap is located on the inside, or both peripheries are butted. It may be detachably composed utilizing screws or the like.

The shape of the blood-filtering material is not restricted, but a disc is preferable in view of production. By rendering the size of the blood-filtering material slightly greater than the inside section of the holder body (i.e. filter chamber), leakage of blood at the periphery of the filtering material can be prevented. To render the shape square is also preferable because of no generation of cutting loss.

A communicating needle connects the blood-filtering unit to the vacuum blood-drawing tube by running through a sealant. The communicating needle is firmly connected to the exit of the filtrate passage at the opposite side of the inlet of the blood-filtering unit by a means selected from those described above to connect the blood-drawing needle to the blood inlet. It may have a stopper such as a projection to control its length going into the vacuum blood-drawing tube. With the stopper the distance between the blood-filtering unit and the vacuum blood-drawing tube is kept constant to make handling simple.

By utilizing vacuum, the vacuum blood-drawing tube performs blood drawing, blood filtering and reception of filtered plasma, successively. The shape of the vacuum blood-drawing tube is not restricted, but a cylinder type is preferable. However, a tube of an ellipsoid or a polygon, a sphere or a spheroid may be permissible if it keeps a necessary reception volume. On the other hand, the distance between the plane on which the blood-drawing needle fixed and the bottom of the vacuum blood-drawing tube is about 2–20 cm, preferably about 5–15 cm before use in view of better handling, especially one-handed handling. The volume of the vacuum blood-drawing tube is 1–20 ml, preferably 2–10 ml.

The vacuum blood-drawing tube is preferably made of material which does not have any effect on blood with considerable hardness and transparency, since the inside of the tube is desirably to be seen from outside. To give actual examples, it is preferably made of glass or such plastics as polystyrene, polymethacrylates, polyethylene, polypropylene, polyesters, nylon or polycarbonates.

The vacuum blood-drawing tube has at least one opening sealed by the sealant to keep the inside of the tube in vacuum. The sealant is made of a mono- or multi-layer sheet composed of a rubber sheet (e.g. a sheet of natural rubber, synthetic rubber or silicone rubber), a metal film (e.g. an aluminum film), a laminated plastic sheet (e.g. a plastic sheet comprising an aluminum sheet or a deposited aluminum layer) or a plastic sheet (e.g. a polypropylene sheet, a polyvinylidene chloride sheet, a polyester sheet or polyamide sheet). The part of the sealant contacting the periphery of the communicating needle run into the vacuum blood-drawing tube must be kept in airtight during filtration of blood, and so at least an area through where the communicating needle runs into the tube is preferably made of an elastic material. The area is preferably devised to be breakable by the communicating needle with rather low force. The sealant is fit on the vacuum blood-drawing tube by adhesion, fusion welding, compressing, etc. The area through where the communicating needle runs in may be located at the bottom of the vacuum blood-drawing tube, too.

Commercially available vacuum blood-drawing tubes as they are or variations of them in length or diameter etc. may be utilized for the purpose of the present invention.

The expanding and contracting element movably connects the blood-filtering unit with the vacuum blood-drawing tube, and also acts to make the vacuum blood-drawing tube hold the blood-filtering unit and to determine interposition between them, though not much strictly. A bellows or a multi-foldable tube such as a dual-foldable slip tube etc. can be mentioned as examples of the expanding and contracting element. The expanding and contracting element is preferably transparent too. The bellows are preferably made of a rubber or plastic sheet (e.g. a sheet of polyethylene or polyamides) and the multi-foldable tube is preferably made of various plastic sheets (e.g. a sheet of polypropylene, polystyrene, polyesters or polycarbonates). The inside of the expanding and contracting element must be communicated to the outside of it to make expansion and contraction of the element possible. Thus, some air release is provided on the element if necessary. Further, at least one side of the expanding and contracting element, preferably the side connected to the vacuum blood-drawing tube, is preferably connected by compressing, for example, to make the vacuum blood-drawing tube detachable from the blood-filtering unit after the end of filtration. The other side of it may be connected to the blood-filtering unit by compressing, adhesion or fusion welding etc.

Plasma is collected using the blood-filtering unit according to the present invention as follows. At the beginning, the blood-drawing needle is stung into blood vessel in a similar manner as an injection syringe. Then the communicating injection needle is run into the vacuum blood-drawing tube by pushing the expanding and contracting element, holding the periphery of the blood-filtering unit, or around the area at where the blood-drawing needle is fixed, with first finger and long finger, while holding the bottom of the vacuum blood collecting tube with thumb. Thus, the vacuum blood-drawing tube is communicated to the blood-filtering unit to draw blood, filter the blood and collect the filtered plasma in the vacuum blood-drawing tube by the vacuum of the tube. After the end of drawing of blood, the blood-filtering unit and the expanding and contracting element are removed from the vacuum blood-drawing tube to provide the filtered plasma for analysis.

The present invention is described in more detail by referring to the following example.

EXAMPLES

Example 1

FIG. 1 exemplifies a cross sectional drawing of a plasma-collecting device according to the present invention. The plasma-collecting device comprises the blood-filtering unit 1, the vacuum blood-drawing tube 2, and the expanding and contracting element 3 connecting the blood-filtering unit 1 and the vacuum blood-drawing tube 2.

The blood-filtering unit is of a short cylinder comprising the holder 11 of polystyrene having a outer diameter of 17.0 mm containing six glass fiber filters 12, each of which is 0.91 mm thick, and a microporous polysulfone membrane 13 of 15.9 mm in diameter and 150 μm in thickness which is provided on the side of the communicating needle 17. The holder 11 comprises the blood inlet 14 on the side of the blood-drawing needle 16 and the filtrate outlet 15 on the side of the vacuum blood-drawing tube 2, both of which are formed prominent from the holder. The blood-drawing needle 16 and the communicating needle 17 are compressed into the blood inlet 14 and the filtrate outlet 15, respectively. Both needles 16 and 17 are made of stainless steel.

The vacuum blood-drawing tube 2 is composed of a polyethylene terephthalate cylinder having outer diameter of 17.0 mm and content of 10 ml, and is provided with the sealant 21 made of a laminate containing an aluminum thin film on an upper opening. Around the center of the sealant, the run through area 22 made of rubber is provided. The run through area 23 made of rubber is also provided at the bottom of the vacuum blood-drawing tube 2. The inside of the vacuum blood-drawing tube 2 is kept at reduced pressure of around 50~600 mmHg.

The blood-filtering unit 1 is connected with the vacuum blood-drawing tube 2 with the bellows 31 made of polypropylene. The bellows is provided with the air release hole 32. The bellows is fixed to the blood-filtering unit with an adhesive, while is detachably compressed into the vacuum blood-drawing tube 2.

The distance (b) between the front edge of the blood-filtering unit and the bottom of the vacuum blood-drawing tube is 13.0 mm.

Figure 2:
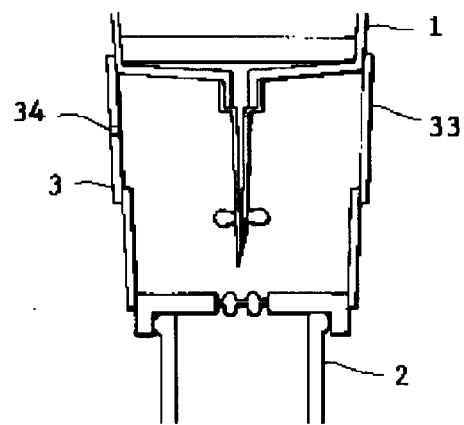
FIG. 2 is a longitudinal section of an expanding and contracting element comprising a dual-foldable tube 33 in the plasma-collecting device in accordance with the present invention.

FIG. 2 is a cross sectional drawing of the contracting and expanding element of the dual-foldable slide tube 33 in place of the bellows 31. The dual-foldable slide tube 33 is made of polystyrene, which is adhered to the blood-filtering unit and is compressed into the vacuum blood-drawing tube. The air release hole 34 is provided on the dual-foldable slide tube 33.

Thus, the present invention renders us drawing and filtering blood instantaneously to obtain a necessary amount of plasma readily and reliably.

What is claimed is:

1. A plasma-collecting device comprising a blood-filtering unit, a vacuum blood-drawing tube with a sealant, and a contracting and expanding element moveably connecting the blood-filtering unit with the vacuum blood-drawing tube, thus allowing the vacuum blood-drawing tube to connect to the blood-filtering unit, wherein a blood-drawing needle is fixed on one side of the blood-filtering unit and a communicating needle is fixed on the other side of the blood-filtering unit, wherein said communicating needle is capable of penetrating into said vacuum blood-drawing tube through said sealant.

2. The plasma-collecting device of claim 1, wherein the contracting and expanding element is a bellows.

3. The plasma-collecting device of claim 1, wherein the contracting and expanding element is a multi-foldable tube.

4. The plasma-collecting device of claim 1, wherein the blood-filtering unit does not have a blood reservoir.

5. The plasma-collecting device of claim 1, wherein the sealant is provided with a thinned portion to form an area for inserting the communicating needle.

6. A plasma-collecting device comprising a blood-filtering unit, a vacuum blood-drawing tube with a sealant, and a contracting and expanding element connecting the blood-filtering unit and the vacuum blood-drawing tube wherein the vacuum blood-drawing tube and the blood-filtering unit are integrated with each other via the contracting and expanding element, thus allowing the vacuum blood-drawing tube to hold the blood-filtering unit, wherein a blood-drawing needle is fixed on one side of the blood-filtering unit and a communicating needle, which is able to penetrate the vacuum blood-drawing tube through the sealant, is fixed on the other side of the blood-filtering unit, and the contracting and expanding element is a bellows.

7. The plasma-collecting device of claim 6, wherein the blood-filtering unit does not have a blood reservoir.

8. The plasma-collecting device of claim 6, wherein the sealant is provided with a thinned portion to form an area for inserting the communicating needle.

* * * * *